United States Patent
Parins

(10) Patent No.: US 7,540,845 B2
(45) Date of Patent: *Jun. 2, 2009

(54) MEDICAL DEVICE COIL

(75) Inventor: David J. Parins, Corcoran, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 907 days.

This patent is subject to a terminal disclaimer.

(21) Appl. No.: 10/656,630

(22) Filed: Sep. 5, 2003

(65) Prior Publication Data

US 2005/0054951 A1 Mar. 10, 2005

(51) Int. Cl.
*A61M 25/00* (2006.01)
*A61M 5/178* (2006.01)

(52) U.S. Cl. .................. 600/585; 604/164.13
(58) Field of Classification Search .......... 600/585; 604/164.13
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 3,789,841 A | 2/1974 | Antoshkiw | |
| 3,973,556 A | 8/1976 | Fleischhacker et al. | |
| 4,538,622 A | 9/1985 | Samson et al. | |
| 4,554,929 A | 11/1985 | Samson et al. | |
| 4,619,274 A | 10/1986 | Morrison | |
| 4,714,815 A | 12/1987 | Swarts et al. | |
| 4,721,117 A | 1/1988 | Mar et al. | |
| 4,763,647 A | 8/1988 | Gambale | |
| 4,846,186 A | 7/1989 | Box et al. | |
| 4,955,862 A | 9/1990 | Sepetka | |
| 4,966,163 A | 10/1990 | Kraus et al. | |
| 5,129,890 A | 7/1992 | Bates et al. | |
| 5,188,621 A | 2/1993 | Samson | |
| 5,222,949 A * | 6/1993 | Kaldany | 604/524 |
| 5,238,004 A | 8/1993 | Sahatjian et al. | |
| 5,267,574 A | 12/1993 | Viera et al. | |
| 5,313,967 A | 5/1994 | Lieber et al. | |
| 5,372,144 A | 12/1994 | Mortier et al. | |
| 5,406,960 A | 4/1995 | Corso, Jr. | |
| 5,415,178 A | 5/1995 | Hsi et al. | |
| 5,497,783 A | 3/1996 | Urick et al. | |
| 5,606,979 A | 3/1997 | Hodgson | |
| 5,606,981 A * | 3/1997 | Tartacower et al. | 600/585 |
| 5,772,609 A | 6/1998 | Nguyen et al. | |
| 5,797,856 A | 8/1998 | Frisbie et al. | |
| 5,830,155 A | 11/1998 | Frechette et al. | |

(Continued)

FOREIGN PATENT DOCUMENTS

EP 1 208 868 5/2002

(Continued)

*Primary Examiner*—Max Hindenburg
*Assistant Examiner*—Jeffrey G Hoekstra
(74) *Attorney, Agent, or Firm*—Crompton, Seager & Tufte, LLC

(57) ABSTRACT

An intracorporal device includes a helically wound coil having a plurality of windings forming a coil length and a thermoplastic polymer sleeve circumferentially disposed about a portion of the coil length. A plurality of discrete affixation points are disposed along the coil length. Each discrete affixation point fixes the thermoplastic polymer sleeve to two or more coil windings.

16 Claims, 1 Drawing Sheet

U.S. PATENT DOCUMENTS

| | | | |
|---|---|---|---|
| 5,882,333 A * | 3/1999 | Schaer et al. | 604/95.01 |
| 5,984,878 A | 11/1999 | Engelson | |
| 6,042,876 A | 3/2000 | Deem | |
| 6,056,702 A | 5/2000 | Lorenzo | |
| 6,061,595 A | 5/2000 | Safarevich | |
| 6,152,912 A * | 11/2000 | Jansen et al. | 604/526 |
| 6,296,616 B1 | 10/2001 | McMahon | |
| 6,312,458 B1 * | 11/2001 | Golds | 623/1.13 |
| 6,373,024 B1 | 4/2002 | Safarevich et al. | |
| 6,508,803 B1 | 1/2003 | Horikawa et al. | |
| 6,849,224 B2 * | 2/2005 | Wang et al. | 264/478 |
| 7,182,735 B2 | 2/2007 | Shireman et al. | |
| 2001/0009980 A1 * | 7/2001 | Richardson et al. | 600/585 |
| 2002/0049392 A1 * | 4/2002 | DeMello | 600/585 |
| 2003/0069520 A1 | 4/2003 | Skujins et al. | |
| 2003/0069521 A1 * | 4/2003 | Reynolds et al. | 600/585 |
| 2003/0149465 A1 | 8/2003 | Heidner et al. | |
| 2004/0167442 A1 | 8/2004 | Shireman et al. | |

FOREIGN PATENT DOCUMENTS

| | | |
|---|---|---|
| EP | 1208868 A2 * | 5/2002 |
| JP | 58-90389 | 5/1983 |
| JP | 59-92188 | 5/1984 |
| JP | 2001229985 A | 8/2001 |
| WO | 2004091440 A1 | 10/2004 |

* cited by examiner

MEDICAL DEVICE COIL

TECHNICAL FIELD

The invention pertains generally to medical device coils useful for a variety of applications such as catheters, guidewires, and the like.

BACKGROUND

A wide variety of medical devices such as catheters and guidewires have been developed. Medical devices such as guidewires can be used in conjunction with devices such as catheters to facilitate navigation through the anatomy of a patient. Because the anatomy of a patient may be very tortuous, it can be desirable to have particular performance features in an elongate medical device. A number of different structures and assemblies for elongate medical devices such as guidewires are known each having certain advantages and disadvantages. However, there is an ongoing need to provide alternative structures and assemblies.

SUMMARY OF SOME EMBODIMENTS

The invention provides several alternative designs, materials and methods of manufacturing alternative medical device structures and assemblies.

Accordingly, an example embodiment of the invention can be found in an intracorporal device that includes a helically wound coil having a plurality of windings forming a coil length and a thermoplastic polymer sleeve circumferentially disposed about a portion of the coil length. A plurality of discrete affixation points disposed along the coil length each fixes the thermoplastic polymer sleeve to two or more coil windings.

Another example embodiment of the invention can be found in an intracorporal device including a helically wound coil having a plurality of windings having an outer perimeter and forming a coil length and a thermoplastic polymer sleeve circumferentially disposed about a portion of the coil length. A plurality of discrete affixation points are disposed on only a portion of the outer perimeter and along the coil length. Each discrete affixation point fixes the thermoplastic polymer sleeve to two or more coil windings.

Another example embodiment of the invention can be found in a medical device including an elongate shaft, a helically wound coil having a plurality of windings forming a coil length disposed about a portion of the elongate shaft and a thermoplastic polymer sleeve circumferentially disposed about a portion of the coil length. A plurality of discrete affixation points are disposed along the coil length. Each discrete affixation point fixes the thermoplastic polymer sleeve to two or more coil windings.

Another example embodiment of the invention can be found in a guidewire including an elongate shaft having a proximal end and an opposing distal end, a helically wound coil having a plurality of windings forming a coil length disposed about a portion of the distal end and a thermoplastic polymer sleeve circumferentially disposed about a portion of the coil length. A plurality of discrete affixation points are disposed along the coil length. Each discrete affixation point fixes the thermoplastic polymer sleeve to two or more coil windings.

Another example embodiment of the invention can be found in a process for forming and intracorporal device including disposing a thermoplastic polymer sleeve circumferentially disposed about a portion of a helically wound coil having a plurality of windings forming a coil length and forming a plurality of discrete affixation points along the coil length. Each discrete affixation point fixes the thermoplastic polymer sleeve to two or more coil windings.

The above summary of some embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
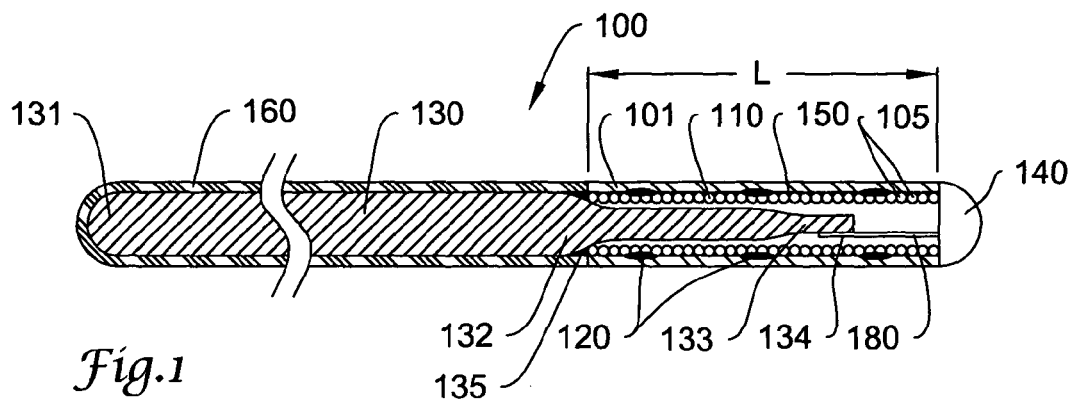
FIG. 1 is a cross-sectional view of a guidewire coil with a plurality of joining elements and a thermoplastic sleeve affixed to the coil with a plurality of discrete affixation points disposed along the coil length.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

For example, although discussed with specific reference to guidewires in the particular embodiments described herein, the invention may be applicable to a variety of medical devices that are adapted to be advanced into the anatomy of a patient through an opening or lumen. For example, the invention may be applicable to fixed wire devices, catheters (e.g. balloon, stent delivery, etc.) drive shafts for rotational devices such as atherectomy catheters and IVUS catheters, endoscopic devices, laproscopic devices, embolic protection devices, spinal or cranial navigational devices, and other such devices. Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

Refer now to FIG. 1, which is a cross-sectional view of a guidewire 100 including a coil 110 with a thermoplastic sleeve 101 affixed to the coil 110 with a plurality of discrete affixation points 120 disposed along the coil length L. The guidewire 100 includes a core 130. The core may have a proximal section 131 and an opposing distal section 132. The distal section 132 can include a series of taper and constant diameter sections as illustrated in FIG. 1. The coil 110 can be disposed about a portion of the core, for example the core distal section 132. A thermoplastic polymer sleeve 101 may be circumferentially disposed about at least a portion of the coil length L. A plurality of discrete affixation points 120 may be disposed along the coil length L. Each affixation point 120 secures or fixes a portion of the thermoplastic polymer sleeve 101 to two or more coil windings 105.

The coil 110 can be formed of a variety of materials including metals, metal alloys, polymers, and the like. Some examples of material for use in the coil 110 include a metal or a metal alloy such as a stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. Some additional examples of suitable material include a polymer material, such as a high performance polymer, and the like.

In some embodiments, the coil 110 or portions thereof can be made of, or coated or plated with, or otherwise include a radiopaque material. Radiopaque materials are understood to be materials capable of producing a relatively bright image on a fluoroscopy screen or another imaging technique during a medical procedure. This relatively bright image aids the user of medical device 100 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, the coil 110, or other portions of the guidewire 100, can include materials or structure to impart a degree of MRI compatibility. For example, to enhance compatibility with Magnetic Resonance Imaging (MRI) machines, it may be desirable to make the coil 110, or other portions of the guidewire 100, in a manner that would impart a degree of MRI compatibility. For example, the elongate shaft or core 130, the coil 110, or portions thereof, or other portions of the guidewire 100, may be made of a material that does not substantially distort the image and create substantial artifacts (artifacts are gaps in the image). Certain ferromagnetic materials, for example, may not be suitable because they may create artifacts in an MRI image. The elongate shaft or core 130, the coil 110, or portions thereof, may also be made from a material that the MRI machine can image. Some materials that exhibit these characteristics include, for example, tungsten, Elgiloy, MP35N, nitinol, and the like, and others, or combinations or alloys thereof.

In some embodiments, the coil 110 can be made of a material that is compatible with the core wire 130 and the distal tip 140. The particular material used can be chosen in part based on the desired flexibility requirements or other desired characteristics. In some particular embodiments, the coil 110 can be formed from a superelastic or linear elastic nickel-titanium alloy, for example, linear elastic or superelastic nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Within the family of commercially available nitinol alloys, is a category designated "super elastic" (i.e. pseudoelastic) and a category designated "linear elastic". Although these two categories of material are similar in chemistry, they each exhibit distinct and useful mechanical properties. Either, or both superelastic and linear elastic nitinol can be used.

One example of a suitable nickel-titanium alloy that may exhibit linear elastic properties is FHP—NT alloy commercially available from Furukawa Techno Material Co. of Kanagawa, Japan. Some examples of suitable nickel-titanium alloys that may exhibit linear elastic characteristics include those disclosed in U.S. Pat. Nos. 5,238,004 and 6,508,803, which are incorporated herein by reference.

The coil 110 can be formed of round or flat ribbon ranging in dimensions to achieve the desired flexibility. It can also be appreciated that other cross-sectional shapes or combinations of shapes may be utilized without departing from the spirit of the invention. For example, the cross-sectional shape of wires or filaments used to make the coil may be oval, rectangular, square, triangle, polygonal, and the like, or any suitable shape. In some embodiments, the coil 110 can be a round ribbon in the range of about 0.001-0.015 inches in diameter, and can have a length in the range of about 0.1 to about 20 inches, however, other dimensions are contemplated.

The coil 110 can be wrapped in a helical fashion by conventional winding techniques. The pitch of adjacent turns of the coil 46 may be tightly wrapped so that each turn touches the succeeding turn or the pitch may be set such that the coil 110 is wrapped in an open fashion.

A thermoplastic polymer sleeve 101 can be disposed circumferentially about at least a portion of the coil 110. The thermoplastic polymer sleeve 101 may be formed from any thermoplastic polymer. A non-limiting listing of thermoplastic polymers includes; polyurethanes, polyamides, polyvinylchloride (PVC), fluorocarbons, polystyrene, polypropylene, polyethylene, polyester and acrylic resins. As these materials are heated, they soften or melt and then harden when cooled.

The thermoplastic polymer sleeve 101 can be fixed or secured to the coil 110 with a plurality of discrete affixation points 120 disposed along the coil length L. Each discrete affixation point 120 fixes the thermoplastic polymer sleeve 101 to two or more windings 105.

Figure 2:
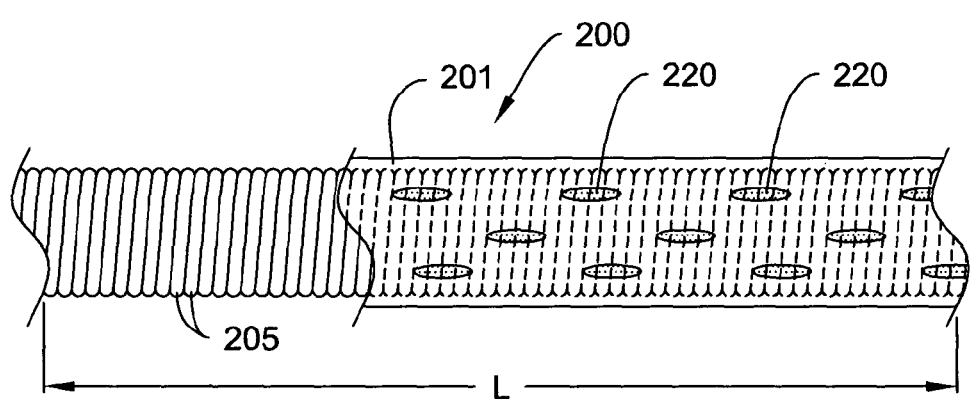
FIG. 2 is a side elevation view of a coil and a thermoplastic sleeve affixed to the coil with a plurality of discrete affixation points disposed along the coil length in accordance with the invention.

Each discrete affixation point 120 may fix or join from 2, 3, 4, 5, 6, 7, 8, 9, or 10 or more coil windings 105 together and to the thermoplastic polymer sleeve 101. There may be 2, 3, 4, 5, 6, 7, 8, 9, 10, 11, 12, 13, 14, 15, 16, 17, 18, 19, 20, 25, 30, 35, 40 or more discrete affixation points 120 disposed in a uniform or non-uniform pattern along the coil length L. In some embodiments, each discrete affixation point 120 may only function to join coil windings 105 to the thermoplastic polymer sleeve 101. The length and width of the affixation points can vary, depending upon the desired characteristics of the device. For example, in some embodiments, each discrete affixation point 120 may have a length in the range of about 0.1 to about 0.3 mm and a width in the range of about 0.1 to about 0.5 mm. The discrete affixation points 120 can be discrete elements aligned orthogonal to the coil windings 105 as illustrated in FIG. 2. The discrete affixation points 120 are formed from the thermoplastic polymer sleeve 101.

The coil windings 105 define an outer perimeter 150. The discrete affixation points 120 can be disposed about the outer perimeter 150 such that only a portion of the outer perimeter 150 is covered by discrete affixation points 120. Each discrete affixation point 120 may be disposed on only a portion of the total outer perimeter 150 of each winding 105, for example, in some embodiments, less than 1/10 off the total outer perimeter 150 of each winding 105. In other words, in at least some embodiments, each discrete affixation point 120 does not extend around the outer perimeter 150 of the coil 110, but rather, fixes or joins to 2 or more coil windings along only a portion of the outer perimeter 150 of the coil 110. As such, each discrete affixation point 120 provides a bond between the thermoplastic polymer sleeve and coil windings to which it is attached, and a bond between the coil windings to which it is attached.

The discrete affixation points 120 can be formed in any suitable manner, including, for example, the selective heating of the thermoplastic polymer sleeve 101 at the desired location for each discrete affixation points 120. Discrete sections or portions of the thermoplastic polymer can be heated until they melt or reflow, allowing portions of the thermoplastic polymer to flow into and/or around an adjoining coil surface. These portions of the thermoplastic polymer can then be allowed to cool and harden in an affixing manner on and/or around an adjoining coil surface.

It is to be appreciated that various heating processes can be utilized without deviating from the spirit and scope of the invention. A variety of heat sources can be used to melt the thermoplastic polymer. Some examples of suitable heating processes or sources can include welding processes or heat sources, for example, LASER welding processes or heat sources, TIG welding processes or heat sources, microplasma welding processes or heat sources, electron beam processes or heat sources, and friction or inertia welding processes or heat sources, soldering processes or heat sources, and the like. In using such processes, the thermoplastic polymer can be heated in the desired patterns to create the discrete affixation points.

In laser welding or laser diode processes or heat sources, a light beam is used to supply the necessary heat. Laser heat sources can be beneficial in some embodiments, as the use of a laser light heat source can in some cases provide pinpoint accuracy.

The discrete affixation points 120 of the thermoplastic polymer sleeve 101 can provide enhanced torque transmission along the coil length L and enhanced pushability while still providing flexibility that a coil 110 offers. This is due at least in part to the bonding of a plurality of coil windings to each other at each discrete affixation point. The degree of enhanced torque transmission and/or push-ability is dependent at least in part on the number of discrete affixation points 120 along the length of the coil, and the size of each discrete affixation points 120 (i.e. the number of coil windings joined be each affixation point 120). Those of skill in the art, and others will recognize that as a general proposition, that greater enhanced torque transmission and/or push-ability can be achieved by using a greater the number of discrete affixation points 120 along a coil length, and/or by increasing the number of coil windings 105 joined by each discrete affixation points 120. The number and size of the discrete affixation points 120 can be varied to obtain the desired characteristics.

The thermoplastic polymer sleeve 101 including the discrete affixation points 120 can be created or disposed on the coil 110 prior to the attachment of the coil 110 to other structure of a device, such as a guidewire, or in some embodiments, can be created or disposed on the coil 110 after attachment of the coil 110 to other structure of the device, such as the core or shaft 130 or the distal tip 140 of a guidewire 100.

Such a coil 110, including the polymer sheath 101 including discrete affixation points 120, as discussed above, can be incorporated into a broad variety of medical devices. For example, as shown in FIG. 1, the coil 110 can be incorporated into a guidewire 100, that may include an elongate shaft or core 130. The coil 110 can be disposed on a portion of the elongate shaft 130, for example, at the distal end 132. It should be understood, however, that such a coil 110, including the polymer sheath 101 including discrete affixation points 120, can be incorporated into a broad variety of medical devices.

With reference to the embodiment shown in FIG. 1, the elongate shaft or core 130 can have a solid cross-section or a hollow cross-section. In other embodiments, the elongate shaft or core 130 can include a combination of areas having solid cross-sections and hollow cross sections. Moreover, the elongate shaft or core 130 can be made of rounded wire, flattened ribbon, or other such structures having various cross-sectional geometries. The cross-sectional geometries along the length of the elongate shaft or core 130 can also be constant or can vary. For example, FIG. 1 depicts the elongate shaft or core 130 as having a generally round cross-sectional shape. It can be appreciated that other cross-sectional shapes or combinations of shapes may be utilized without departing from the spirit of the invention. For example, the cross-sectional shape of the elongate shaft or core 130 may be oval, rectangular, square, polygonal, and the like, or any suitable shape.

In some embodiments, the elongate shaft or core 130 can be formed of any suitable metallic, polymeric or composite material. In some embodiments, part or all of the elongate shaft or core 130 can be formed of a metal or a metal alloy such as a stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. The particular material used can be chosen in part based on the desired flexibility requirements or other desired characteristics or the elongate shaft or core 130. In some particular embodiments, the elongate shaft or core 130 can be formed from a superelastic or linear elastic nickel-titanium alloy, for example, linear elastic or superelastic nitinol, for example, those discussed above with regard to the coil 110.

The entire elongate shaft or core 130 can be made of the same material, or in some embodiments, can include portions or sections that are made of different materials. In some embodiments, the material used to construct different portions of the core wire 130 can be chosen to impart varying flexibility and stiffness characteristics to different portions of the wire. For example, a proximal portion 131 and a distal portion 132 can be formed of different materials (i.e., materials having different moduli of elasticity) resulting in a difference in flexibility. In some embodiments, the material used to construct the proximal portion 131 can be relatively stiff for push-ability and torque-ability, and the material used to construct the distal portion 132 can be relatively flexible by comparison for better lateral track-ability and steer-ability. For example, the proximal portion 131 can be formed of, for example, straightened 304v stainless steel wire, and the distal portion 132 can be formed of, for example, a straightened super elastic or linear elastic alloy (e.g., nickel-titanium) wire.

In embodiments where different portions of elongate shaft or core 130 are made of different material, the different portions can be connected using any suitable connecting techniques. For example, the different portions of the elongate shaft or core 130 can be connected using welding, soldering, brazing, adhesive, or the like, or combinations thereof. Additionally, some embodiments can include one or more mechanical connectors or connector assemblies to connect the different portions of the elongate shaft or core 130 that are made of different materials. The connector may comprise any structure generally suitable for connecting portions of a elongate shaft or core 130. One example of a suitable structure includes a structure such as a hypotube or a coiled wire which has an inside diameter sized appropriately to receive and connect the different portions of the elongate shaft or core 130. Some methods and structures that can be used to interconnect different shaft sections are disclosed in U.S. patent application Ser. Nos. 09/972,276, and 10/086,992, which are incorporated herein by reference.

In at least some embodiments, portions or all of the elongate shaft or core 130, the coil 110, or other structures included within the medical device 100 may also be doped with, coated or plated with, made of, or otherwise include a radiopaque material. Additionally, in some embodiments, a degree of MRI compatibility can be imparted into the medical device 100, as discussed above.

The elongate shaft or core 130 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of the elongate shaft or core 130 may be tapered and the taper can be in either the proximal or the distal direction. The number, arrangement, size, and length of the tapering and constant diameter portions can be varied to achieve the desired characteristics, such as flexibility and torque transmission characteristics. In some other embodiments, a guidewire core wire 130 can have a profile in which the core wire has a greater number of constant diameter sections, separated by a greater number of taper sections. In some embodiments, a guidewire core wire 130 can have fewer or no tapers. The tapers can be as illustrated in FIG. 1, or they can be longer (more gradual), or shorter (less gradual).

The guidewire 100 shown in FIG. 1 also includes a wire or ribbon 180 and a distal tip 140. A wire or ribbon 180 can be disposed between the distal tip 140 and core 130. The wire or ribbon 180 can be attached adjacent the distal end 132 of the core 130, and extend distally to the distal tip 140. In some embodiments, the wire or ribbon 180 can be a fabricated or formed wire structure, for example a coiled or wound wire or ribbon. In the embodiment shown, the ribbon 180 is a generally straight ribbon that overlaps with and is attached to the constant diameter region 133 at attachment point 134. In some embodiments, the ribbon 180 overlaps with the constant diameter section 133 by a length in the range of about 0.05 to 1.0 inch, but in other embodiments, the length of the overlap can be greater or less.

The ribbon 180 can be made of any suitable material and sized appropriately to give the desired characteristics, such as strength and flexibility characteristics. Some examples of suitable materials include metals, metal alloys, polymers, and the like. In some embodiments, the ribbon 180 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire. The ribbon 180 can be attached using any suitable attachment technique. Some examples of attachment techniques include soldering, brazing, welding, adhesive bonding, crimping, or the like. In some embodiments, the ribbon or wire 180 can function as a shaping structure or a safety structure.

The distal tip 140 can be formed from a variety of different materials, depending on desired performance characteristics. In some embodiments, the distal tip can form an atraumatic portion on the distal end of the device 100. In some embodiments, the distal tip 140 can be formed of a material such as a metallic material that is amenable to being welded, soldered, or otherwise attached to the distal end 132 of the elongate shaft or core 130. For example, in some embodiments, the distal tip 140 can be a solder tip that is disposed via soldering at the distal end of the device and forms an atraumatic rounded portion. In other embodiments, the distal tip can be prefabricated, or partially prefabricated, structure that is thereafter attached to the distal end of the device using suitable attachment techniques, such as welding, soldering, brazing, crimping, friction fitting, adhesive bonding, mechanical interlocking and the like. A variety of different processes, such as soldering, deep drawing, roll forming or metal stamping, metal injection molding, casting and the like, can be used to form the distal tip 140.

In some embodiments, it may be beneficial, but not always necessary, that the distal tip 140 to be formed of a material that is compatible with the particular joining technique used to connect the tip 140 to the other structure. For example, in some particular embodiments, it can be beneficial but not necessary for the distal tip 140 to be formed of the same metal or metal alloy as the distal end 132 of the elongate shaft or core 130. For example, if the elongate shaft or core 130 is formed of stainless steel, it can be beneficial for the distal tip 140 to be formed of stainless steel. In other embodiments, both of the distal tip 140 and the distal end 132 of the elongate shaft or core 130 can be formed of the same metal alloy, such as nitinol.

A guidewire 100 in accordance with some embodiments can optionally include one or more additional coating layers, for example, coating layer 160. Such a coating layer can be the same or different from the material used to make the polymer sleeve 101, and can be disposed over all or part of the guidewire assembly 100. In the embodiment shown in FIG. 1, the coating layer 160 extends over the proximal section of the core wire 130. In some embodiments, the coating layer 160 may be a hydrophilic, protective, lubricious, or other type of coating to perform a desired purpose. Hydrophobic coatings such as fluoropolymers can provide a dry lubricity which can improve guide wire handling and device exchanges. Lubricious coatings can improve steerability and improve lesion crossing capability. Suitable lubricious polymers are well known in the art and may include examples of hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion of the guidewire is coated with a hydrophilic polymer and the more proximal portion 131 is coated 160 with a fluoropolymer, such as polytetrafluroethylene (PTFE).

To form the guidewire 100 shown in FIG. 1, the ribbon can be positioned and attached proximate the elongate shaft or core 130 as illustrated. The ribbon 180 can be secured to the elongate shaft or core 130 in any suitable manner, including for example welding, soldering, brazing, crimping, friction fitting, adhesive bonding, mechanical interlocking and the like. Additionally, the coil 110 can be positioned proximate the elongate shaft or core 130 as illustrated. The coil 110 can be secured to the elongate shaft or core 130 in any suitable manner, including for example welding, soldering, brazing, crimping, friction fitting, adhesive bonding, mechanical interlocking and the like. In the embodiment shown, the coil 110 can be secured at its proximal end to the elongate shaft or core 130 at a proximal attachment point 135, and can be secured at its distal end to the ribbon 180 via the distal tip 140. In some embodiments, the distal tip 140 is a solder tip or a weld tip that is soldered or welded to the ribbon 180 and the coil 110, and forms an atraumatic tip. In other embodiments, the distal tip 140 is prefabricated, or partially prefabricated, and is connected to the ribbon 180 and the coil 110 using a suitable attachment technique.

In some embodiments, the coil 110 and/or the ribbon 180 can be welded to the elongate shaft or core 130, and the distal tip 140 can be welded to the coil 110 and/or the ribbon 180. It is to be appreciated that various welding processes can be utilized without deviating from the spirit and scope of the invention. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment that may be suitable in some embodiments is commercially available from Unitek Miyachi of Monrovia, Calif. and Rofin-Sinar Incorporated of Plymouth, Mich. Resistance welding equipment that may be useful in some embodiments is commercially available from Palomar Products Incorporated of Carlsbad, Calif. and Polaris Electronics of Olathe, Kans. TIG welding equipment that may be useful in some embodiments is commercially available from Weldlogic Incorporated of Newbury Park, Calif. Microplasma welding equipment that may be useful in some embodiments is commercially available from Process Welding Systems Incorporated of Smyrna, Tenn.

In some embodiments, laser or plasma welding can be used to secure one or more of the distal tip 140, the coil 110, the ribbon 180 and/or the elongate shaft or core 130 securely together. It should be understood, however, that other attachment techniques may be used instead, or in combination. In laser welding, a light beam is used to supply the necessary heat. Laser welding can be beneficial in the processes contemplated by the invention, as the use of a laser light heat source can provide pinpoint accuracy. In some embodiments, laser diode soldering can be useful.

As indicated above, the thermoplastic polymer sleeve 101 including the discrete affixation points 120 can be created or disposed on the coil 110 prior to the attachment of the coil 110 to other structure of a device, such as a guidewire 100, or in some embodiments, can be created or disposed on the coil 110 after attachment of the coil 110 to other structure of the device, such as the core or shaft 130 or the distal tip 140 of a guidewire 100.

It should also be understood that the guidewire 100 can include additional structure, such as additional shaping or safety wires or ribbons, marker bands and/or coils, additional inner or outer coils, inner or outer sheaths or coatings, and the like. Those of skill in the art and others will recognize how to incorporate such additional structures into the device, as is generally known.

FIG. 2 is a side elevation view of a coil 200 and a thermoplastic polymer sleeve 201 disposed over a portion of the coil 200 and including a plurality of discrete affixation points 220. The plurality of discrete affixation points 220 may form a uniform or non-uniform pattern along the coil length L. This plurality of discrete affixation points 220 may have a density of joining elements 220 per unit length that decreases or increases along the coil length L. Decreasing and/or increasing the density of discrete affixation points 220 per unit along the coil length L provides the ability to modify flexibility, torque transmission and pushability as a function of position along the coil length L. For example, a higher density of discrete affixation points 220 at one portion along the length of the coil can provide that portion of the coil 200 with higher torque transfer and pushability relative to another portion along the length of the coil that has a lower density of discrete affixation points 220. For example, a higher density of discrete affixation points 220 at a proximal end of the coil can provide a coil 200 with high torque transfer at the proximal end and higher flexibility at a distal end of the coil 200. It should be understood that this is only one example embodiment, and that the density of discrete affixation points 220 per unit along the coil length L can be modified, for example such that the density is higher near the distal end, or such that the density is higher near the middle of the coil, or such that the density varies along the length of the coil, and the like.

Figure 3:
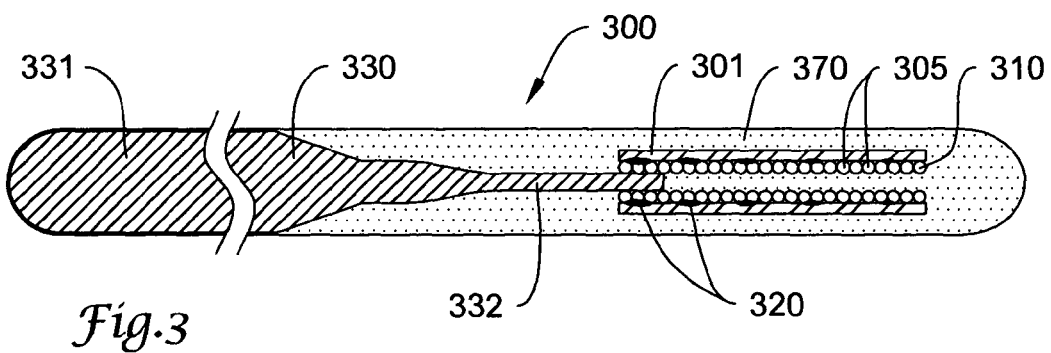
FIG. 3 is a cross-sectional view of an alternative guidewire with a coil and a thermoplastic sleeve affixed to the coil with a plurality of discrete affixation points disposed along the coil length in accordance with the invention.

FIG. 3 is a cross-sectional view of an alternative guidewire 300 with a coil 310 and a thermoplastic polymer sleeve 301 disposed over a portion of the coil 310 and including a plurality of discrete affixation points 320. The coil 310 is disposed over a portion of the core 330 and the thermoplastic polymer sleeve 301 is disposed over a portion of the coil 310. A polymer sheath 370 is disposed over the core 330, coil 310 and sleeve 301.

In this embodiment a polymer tip guidewire 300 is formed by including the polymer sheath 370 that forms a rounded tip over the coil 310. The polymer sheath 370 can be made from any material that can provide the desired strength, flexibility or other desired characteristics.

The use of a polymer sheath 370 in some embodiments can serve several functions, such as imparting desired flexibility or lubricious properties to the guidewire assembly. Choice of polymers for the sheath 370 will vary, depending upon the desired characteristics. For example, polymers with a low durometer or hardness will make a very flexible or floppy tip. Conversely, polymers with a high durometer will make a tip which is stiffer. The use of polymers for the sleeve can also provide an atraumatic tip for the guidewire. An atraumatic tip is better suited for passing through fragile body passages. Finally, a polymer can act as a binder for radiopaque materials, as discussed in more detail below.

Some examples of suitable polymer material may include any of a broad variety of polymers generally known for use as guidewire polymer sheath. In some embodiments, the polymer material used is a thermoplastic polymer material. Some examples of some suitable materials include polyurethane, elastomeric polyamides, block polyamide/ethers (such as Pebax), silicones, and co-polymers. The sheath may be a single polymer, multiple layers, or a blend of polymers. By employing selection of materials and processing techniques, thermoplastic, solvent soluble, and thermosetting variants of these materials can be employed to achieve the desired results.

Further examples of suitable polymeric materials include but are not limited to poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamid, poly(hydroxyethyl methacrylate), polyurethane, polysiloxane and their copolymers.

In some embodiments, the sheath 370, or portions thereof, can include, or be doped with, radiopaque material to make the sheath 370, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the sheath 370 can include a distal section having a higher level of radiopaque material loading, and a proximal section having a correspondingly lower level of loading.

In some embodiments, it is also contemplated that a separate radiopaque member or a series of radiopaque members, such as radiopaque coils, bands, tubes, or other such structures could be attached to the guidewire core wire 330, or incorporated into the core wire by plating, drawing, forging, or ion implantation techniques.

The sheath 370 can be disposed around and attached to the guidewire assembly 300 using any suitable technique for the particular material used. In some embodiments, the sheath 370 can be attached by heating a sleeve of polymer material to a temperature until it is reformed around the guidewire assembly 300. In some other embodiments, the sheath 370 can be attached using heat shrinking techniques. In other embodiments, the sheath 370 can be co-extruded with the core wire 330 and other structure. The sheath 370 can be finished, for example, by a centerless grinding or other method, to provide the desired diameter and to provide a smooth outer surface.

One of skill will recognize that a guidewire core wire can have a profile different from that illustrated in FIGS. 1 and 3. For example, the core wire 130, 330 can be continuously tapered, can have a tapered section or a number or series of tapered sections of differing diameters, or can have a constant diameter. In some embodiments, core wire 130, 330 is tapered or otherwise formed to have a geometry that decreases in cross sectional area toward the distal end thereof. If tapered, core wire can include a uniform or a non-uniform transition of the sections, depending on the transition characteristics desired. For example, core wire may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

Similar to what is described above, the structure used to construct the core wire 130, 330 can be designed such that a proximal portion 131, 331 is relatively stiff for pushability and torqueability, and distal portion 132, 332 is relatively flexible by comparison for better lateral trackability and steerability. For example, in some embodiments, a proximal portion 131, 331 has a constant or generally uniform diameter along its length to enhance stiffness. However, embodiments including a proximal portion 131, 331 having a tapered portion or a series of tapered portions are also contemplated. The diameter of the proximal portion 131, 331 can be sized appropriately for the desired stiffness characteristics dependent upon the material used. For example, in some embodiments, a proximal portion 131, 331 can have a diameter in the range of about 0.010 to about 0.025 inches or greater, and in some embodiments, in the range of about 0.010 to about 0.018 inches or greater.

A distal portion 132, 332 can likewise be constant diameter, can be continuously tapered, or can have a tapered section or a number or a series of tapered sections of differing diameters. In embodiments where the structure of core wire 130, 330 is designed such that a distal portion 132, 332 is relatively flexible by comparison to the proximal portion 131, 331 the distal portion 132, 332 can include at least one tapered or reduced diameter portion for better flexibility characteristics.

The lengths of the proximal portions 131, 331, and distal portions 132, 332 are typically, but not always dictated by the length and flexibility characteristics desired in the final medical device. In some embodiments, the proximal portion 131, 331 can have a length in the range of about 50 to about 300 centimeters, and the distal portion 132, 332 can have a length in the range of about 3 to about 50 centimeters.

The core wire 130, 330 can have a solid cross-section as shown, but in some embodiments, can have a hollow cross-section. In yet other embodiments, core wire 130, 330 can include a combination of areas having solid cross-sections and hollow cross sections.

The tapered and constant diameter portions can be formed by any one of a number of different techniques, for example, by centerless grinding, stamping and the like. A centerless grinding technique can utilize an indexing system employing sensors (e.g., optical/reflective, magnetic) to avoid excessive grinding. In addition, the centerless grinding technique can utilize a CBN or diamond abrasive grinding wheel that is well shaped and dressed to avoid grabbing the core wire 130, 330 during the grinding process.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

I claim:

1. An intracorporal device comprising:
    a) a helically wound coil having a plurality of windings forming a coil length;
    b) a thermoplastic polymer tube disposed about a portion of the coil length;
    c) a plurality of discrete affixation points disposed along the coil length wherein each discrete affixation point fixes the thermoplastic tube to two or more coil windings, wherein each discrete affixation point is separate from other discrete affixation points by areas where the thermoplastic polymer tube is not affixed to the coil, wherein the plurality of discrete affixation points includes 10 discrete affixation points disposed along the coil length.

2. An intracorporal device comprising:
    a) a helically wound coil having a plurality of windings forming a coil length;
    b) a thermoplastic polymer tube disposed about a portion of the coil length;
    c) a plurality of discrete affixation points disposed along the coil length wherein each discrete affixation point fixes the thermoplastic tube to two or more coil windings, wherein each discrete affixation point is separate from other discrete affixation points by areas where the thermoplastic polymer tube is not affixed to the coil, wherein the plurality of discrete affixation points form a non-uniform pattern along the coil length, wherein the plurality of discrete affixation points has a density of discrete affixation points per unit length of coil that decreases along the coil length.

3. An intracorporal device comprising:
    a) a helically wound coil having a plurality of windings having an outer perimeter and forming a coil length;
    b) a thermoplastic polymer tube circumferentially disposed about a portion of the coil length;
    c) a plurality of discrete affixation points, each of the affixation points disposed about only a portion of the outer perimeter of the helically wound coil and along a portion of the coil length, wherein each discrete affixation point fixes the thermoplastic tube to two or more coil windings, wherein each discrete affixation point is separated from other discrete affixation points by areas where the polymer tube is not affixed to the coil; and
    wherein the plurality of discrete affixation points includes 10 discrete affixation points disposed along the coil length.

4. An intracorporal device comprising:
    a) a helically wound coil having a plurality of windings having an outer perimeter and forming a coil length;
    b) a thermoplastic polymer tube circumferentially disposed about a portion of the coil length;
    c) a plurality of discrete affixation points, each of the affixation points disposed about only a portion of the outer perimeter of the helically wound coil and along a portion of the coil length, wherein each discrete affixation point fixes the thermoplastic tube to two or more coil windings, wherein each discrete affixation point is separated from other discrete affixation points by areas where the polymer tube is not affixed to the coil;
    wherein the plurality of discrete affixation points form a non-uniform pattern along the coil length; and
    wherein the plurality of discrete affixation points has a density of discrete affixation points per unit length of coil that decreases along the coil length.

5. A medical device comprising:
    a) an elongate shaft;
    b) a helically wound coil having a plurality of windings forming a coil length disposed about a portion of the elongate shaft;
    c) a thermoplastic polymer tube circumferentially disposed about a portion of the coil length; and
    d) a plurality of discrete affixation points disposed along the coil length, wherein each discrete affixation point fixes the thermoplastic polymer tube to two or more coil windings, wherein each discrete affixation point is separated from other discrete affixation points by areas where the polymer tube is not affixed to the coil, wherein the plurality of discrete affixation points includes 10 discrete affixation points disposed along the coil length.

6. A medical device comprising:
    a) an elongate shaft;
    b) a helically wound coil having a plurality of windings forming a coil length disposed about a portion of the elongate shaft;
    c) a thermoplastic polymer tube circumferentially disposed about a portion of the coil length; and
    d) five or more discrete affixation points disposed along the coil length, wherein each discrete affixation point fixes the thermoplastic polymer tube to two or more coil windings, wherein each discrete affixation point is separated from other discrete affixation points by areas where the polymer tube is not affixed to the coil.

7. The medical device according to claim 6, wherein the plurality of discrete affixation points form a non-uniform pattern along the coil length.

8. The medical device according to claim 6, wherein the plurality of discrete affixation points form a uniform pattern along the coil length.

9. The medical device according to claim 6, wherein each discrete affixation point fixes 3 to 10 coil windings to the thermoplastic tube.

10. The medical device according to claim 6, wherein each discrete affixation point is a discrete element aligned orthogonal to the windings.

11. The medical device according to claim 6, wherein each discrete affixation point is a element having a width of 0.1 to 0.5 mm and a length of 0.1 to 0.3 mm.

12. The medical device of claims 6, wherein the medical device comprises a guidewire;
    the elongate shaft has a proximal end and an opposing distal end; and
    the helically wound coil is disposed about a portion of the distal end.

13. A medical device comprising:
a) an elongate shaft;
b) a helically wound coil having a plurality of windings forming a coil length disposed about a portion of the elongate shaft;
c) a thermoplastic polymer tube circumferentially disposed about a portion of the coil length; and
d) a plurality of discrete affixation points disposed along the coil length, wherein each discrete affixation point fixes the thermoplastic polymer tube to two or more coil windings, wherein each discrete affixation point is separated from other discrete affixation points by areas where the polymer tube is not affixed to the coil, wherein the plurality of discrete affixation points form a non-uniform pattern along the coil length, wherein the plurality of discrete affixation points has a density of discrete affixation points per unit length of coil that decreases along the coil length.

14. A guidewire comprising:
a) an elongate shaft having a proximal end and an opposing distal end;
b) a helically wound coil having a plurality of windings forming a coil length disposed about a portion of the distal end;
c) a thermoplastic tube circumferentially disposed about a portion of the coil length; and
d) a plurality of discrete affixation points disposed along the coil length, wherein each discrete affixation point fixes the thermoplastic polymer tube to two or more coil windings, wherein each discrete affixation point is separated from the other discrete affixation points by areas where the polymer tube is not affixed to the coil, wherein the plurality of discrete affixation points form a non-uniform pattern along the coil length.

15. A guidewire comprising:
a) an elongate shaft having a proximal end and an opposing distal end;
b) a helically wound coil having a plurality of windings forming a coil length disposed about a portion of the distal end;
c) a thermoplastic tube circumferentially disposed about a portion of the coil length; and
d) a plurality of discrete affixation points disposed along the coil length, wherein each discrete affixation point fixes the thermoplastic polymer tube to two or more coil windings, wherein each discrete affixation point is separated from the other discrete affixation points by areas where the polymer tube is not affixed to the coil, wherein the plurality of discrete affixation points form a non-uniform pattern along the coil length, wherein the plurality of discrete affixation points has a density of discrete affixation points per unit length that decrease along the coil length.

16. The guidewire according to claim 15, wherein the plurality of discrete affixation points has a density of discrete affixation points per unit length that decrease along the coil length, wherein the thermoplastic polymer tube has a proximal end and a distal end and where the density of discrete affixation points per unit length decreases from the proximal end to the distal end.

* * * * *